United States Patent
Chen

(10) Patent No.: US 11,963,919 B1
(45) Date of Patent: *Apr. 23, 2024

(54) CERVICAL TRACTION PILLOW

(71) Applicant: PLESON (HK) TECHNOLOGY LIMITED, Hongkong (HK)

(72) Inventor: Xin Chen, Hongkong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/471,032

(22) Filed: Sep. 20, 2023

Related U.S. Application Data

(63) Continuation-in-part of application No. 18/082,196, filed on Dec. 15, 2022, now Pat. No. 11,793,334.

(51) Int. Cl.
| | |
|---|---|
| *A61H 1/02* | (2006.01) |
| *A47G 9/10* | (2006.01) |
| *A61F 5/05* | (2006.01) |
| *A61F 7/00* | (2006.01) |
| *A61F 7/08* | (2006.01) |
| *A61H 23/02* | (2006.01) |

(52) U.S. Cl.
CPC ......... *A61H 1/0218* (2013.01); *A47G 9/1036* (2013.01); *A47G 9/1081* (2013.01); *A61F 5/05* (2013.01); *A61F 7/08* (2013.01); *A61H 23/0254* (2013.01); *A61F 2007/0012* (2013.01); *A61F 2007/0086* (2013.01); *A61F 2007/0094* (2013.01); *A61H 2201/0192* (2013.01); *A61H 2201/0207* (2013.01); *A61H 2201/0264* (2013.01); *A61H 2201/1611* (2013.01); *A61H 2201/5097* (2013.01); *A61H 2205/04* (2013.01)

(58) Field of Classification Search
CPC ...... A47G 9/10; A47G 9/1036; A47G 9/1072; A47G 9/1081; A47G 2200/16; A61H 1/0218; A61H 23/0254; A61H 2201/0192; A61H 2201/0207; A61H 2201/0264; A61H 2201/1611; A61H 2201/5097; A61H 2205/04; A61F 5/05; A61F 7/08; A61F 2007/0012; A61F 2007/0086; A61F 2007/0094

See application file for complete search history.

(56) References Cited

U.S. PATENT DOCUMENTS

| | | | | |
|---|---|---|---|---|
| 2,800,897 | A * | 7/1957 | Ross | A61H 23/0263 5/915 |
| 4,858,259 | A * | 8/1989 | Simmons | F25D 3/08 5/923 |
| 5,533,218 | A * | 7/1996 | Fahy | A47C 27/16 5/636 |
| 6,159,169 | A * | 12/2000 | Lambden | A61F 7/08 601/39 |

(Continued)

*Primary Examiner* — Justin C Mikowski
*Assistant Examiner* — George Sun

(57) ABSTRACT

The present disclosure provides a cervical traction pillow includes a cervical traction pillow main body and a heating device. The heating device covers the cervical traction pillow main body. The cervical traction pillow main body is a flexible cervical traction pillow main body with a narrow upper part and a wide lower part, so as to form a neck brace traction portion at an upper end and a base at a lower end, a first back portion connected between the neck brace traction portion and the base, and two first side portions opposite and connected to the neck brace traction portion, the base, and the back portion. The neck brace traction portion and a bottom surface of the base are connected in an acute angle.

19 Claims, 6 Drawing Sheets

(56) References Cited

U.S. PATENT DOCUMENTS

| | | | |
|---|---|---|---|
| 10,201,240 B1* | 2/2019 | Arrighi | A47G 9/1054 |
| 2007/0251013 A1* | 11/2007 | Borror | A01K 1/0353 |
| | | | 5/652 |
| 2011/0275966 A1* | 11/2011 | Alkhattaf | A47G 9/1027 |
| | | | 5/644 |
| 2014/0310877 A1* | 10/2014 | Sternlight | A47G 9/02 |
| | | | 5/639 |
| 2015/0150391 A1* | 6/2015 | Hsu | A47G 9/10 |
| | | | 5/636 |
| 2015/0257541 A1* | 9/2015 | Lazakis | A61F 7/007 |
| | | | 5/421 |
| 2015/0257554 A1* | 9/2015 | Ross | A47G 9/0215 |
| | | | 5/639 |
| 2015/0297003 A1* | 10/2015 | Ahroon | G06T 7/33 |
| | | | 206/38 |
| 2017/0071349 A1* | 3/2017 | Wong | A47C 7/383 |
| 2017/0246970 A1* | 8/2017 | Maddocks | B60N 2/5664 |
| 2018/0289183 A1* | 10/2018 | Karl | A47C 7/383 |
| 2019/0082867 A1* | 3/2019 | Huang | A47G 9/1036 |
| 2020/0037798 A1* | 2/2020 | Nardo | A47G 9/10 |
| 2021/0030174 A1* | 2/2021 | Romo | A47G 9/1081 |

* cited by examiner

CERVICAL TRACTION PILLOW

CROSS-REFERENCE TO RELATED APPLICATIONS

This application is a Continuation-in-Part of the U.S. application Ser. No. 18/082,196 filed on 2022 Dec. 15, and entitled "PROTECTIVE CASE OF CERVICAL TRACTION PILLOW AND CERVICAL TRACTION PILLOW," now pending, the entire disclosures of which are incorporated herein by reference.

TECHNICAL FIELD

The present disclosure relates to the field of traction pillows, in particular to a cervical traction pillow.

BACKGROUND

Cervical traction is a main measure to relieve the symptoms of cervical spondylosis because effective traction can relieve the compression of nerves, blood vessels and spinal cord, and quickly relieve the symptoms of the cervical spondylosis. At present, pillows with a cervical traction function on the market can be used for cervical traction when a user takes a rest, but there are the following problems: First, since a user often uses a cervical traction pillow for cervical traction, the cervical traction pillow easily gets dirty and breeds bacteria after being used for multiple times, and are hard to clean. Second, the current cervical traction pillow can only simply drive the neck to do traction exercises, but cannot accelerate the blood circulation of the cervical vertebra, resulting in a poor effect of cervical traction. Therefore, there is an urgent need to provide a cervical traction pillow, which can prevent the cervical traction pillow from getting dirty, accelerate the blood circulation of the cervical vertebra while the cervical traction pillow drives the cervical vertebra to do traction exercises, improve the cervical traction effect, and relieve the fatigue of the cervical vertebra.

SUMMARY

In order to overcome the shortcomings of the prior art, the present disclosure provides a cervical traction pillow, which can prevent the cervical traction pillow from getting dirty, accelerate the blood circulation of the cervical vertebra while the cervical traction pillow drives the cervical vertebra to do traction exercises, improve the cervical traction effect, and relieve the fatigue of the cervical vertebra.

The technical solution adopted by the present disclosure to solve the technical problem is as follows.

A cervical traction pillow includes a cervical traction pillow main body and a heating device, wherein the heating device covers the cervical traction pillow main body; the cervical traction pillow main body is a flexible cervical traction pillow main body with a narrow upper part and a wide lower part, so as to form a neck brace traction portion at an upper end and a base at a lower end, a first back portion connected between the neck brace traction portion and the base, and two first side portions opposite and connected to the neck brace traction portion, the base, and the back portion; and the neck brace traction portion and a bottom surface of the base are connected in an acute angle.

As the improvement of the present disclosure, the back portion is provided with an adjustment gap; and the adjustment gap is configured to adjust an angle and distance between the neck brace traction portion and the base, so as to adjust a height and supporting angle of the cervical traction pillow main body.

As the improvement of the present disclosure, the heating device covers the neck brace traction portion.

As the improvement of the present disclosure, the cervical traction pillow further includes a traction protective case main body, wherein the traction protective case main body includes a bottom portion, a neck brace protection portion connected to the bottom portion, a second back portion connected between the neck brace protection portion and the bottom portion, and two second side portions opposite and connected to the neck brace protection portion, the bottom portion, and the second back portion; and the neck brace protection portion and the bottom portion are connected in an acute angle.

As the improvement of the present disclosure, the neck brace protection portion includes an inner layer and an outer layer; a first accommodating cavity is formed between the inner layer and the outer layer; and the heating device is arranged in the first accommodating cavity and extends from one end, close to the bottom portion, of the neck brace protection portion to the other end, close to the second back portion, of the neck brace protection portion.

As the improvement of the present disclosure, the traction protective case main body is provided with a second accommodating cavity; the second accommodating cavity fully accommodates the cervical traction pillow main body; the heating device is arranged between the neck brace protection portion and the cervical traction pillow main body and extends from one end, close to the bottom portion, of the neck brace traction portion to the other end, close to the first back portion, of the neck brace traction portion.

As the improvement of the present disclosure, the traction protective case main body, the heating device, and the cervical traction pillow main body are stacked in sequence.

As the improvement of the present disclosure, the cervical traction pillow is further provided with a vibration device; the cervical traction pillow main body is provided with a motor accommodating slot; the vibration device is arranged in the motor accommodating slot; and the vibration device is configured to drive the cervical traction pillow main body to vibrate to achieve a massage function.

As the improvement of the present disclosure, the vibration device is a polarization motor; the polarization motor is provided with a rotating shaft and an eccentric block; and the polarization motor rotates the rotating shaft to drive the eccentric block to ceaselessly strike an inner wall of the motor accommodating slot, so that the polarization motor drives the cervical traction pillow main body to vibrate to achieve the massage function.

As the improvement of the present disclosure, the polarization motor rotates the rotating shaft to drive the eccentric block to ceaselessly strike an inner side wall of the motor accommodating slot, so that the polarization motor drives the cervical traction pillow main body to vibrate to achieve the massage function.

As the improvement of the present disclosure, the polarization motor rotates the rotating shaft to drive the eccentric block to ceaselessly strike a bottom wall of the motor accommodating slot, so that the polarization motor drives the cervical traction pillow main body to vibrate to achieve the massage function.

As the improvement of the present disclosure, the cervical traction pillow further includes a power supply module, wherein the power supply module is electrically connected to the heating device and the vibration device to supply power to the heating device and the vibration device.

As the improvement of the present disclosure, the cervical traction pillow further includes a temperature control device, wherein the temperature control device is electrically connected with the heating device; the temperature control device is configured to control a surface temperature of the heating device; the temperature control device is a temperature control switch; and the temperature control switch is configured to control a current flowing through the heating device to control the surface temperature of the heating device.

As the improvement of the present disclosure, the traction protective case main body is further provided with a power input port; the power input port is electrically connected to the vibration device and the heating device to supply power to the vibration device and the heating device; and the power input port is arranged on one side portion of the two side portions.

As the improvement of the present disclosure, the cervical traction pillow further includes a wireless communication module, wherein the wireless communication module is electrically connected with the temperature control device to receive a wireless temperature control signal and control the surface temperature of the heating device.

As the improvement of the present disclosure, the neck brace traction portion is provided with several massage convex points; a power supply accommodating slot is arranged in the base; and the power supply module is arranged in the power supply accommodating slot.

As the improvement of the present disclosure, the back portion of the cervical traction pillow main body is of a "C"-shaped structure.

As the improvement of the present disclosure, the back portion of the traction protective case main body is of a "C"-shaped structure.

As the improvement of the present disclosure, the traction protective case main body sleeves and covers a surface of the cervical traction pillow main body through a sleeving opening located on one of the two second side portions; and a zipper for opening or closing the sleeving opening is arranged at the sleeving opening.

As the improvement of the present disclosure, the heating device is a graphene heating sheet or a carbon fiber heating sheet or a composite fiber heating piece.

Beneficial effects: the present disclosure provides a cervical traction pillow includes a cervical traction pillow main body and a heating device. The heating device covers the cervical traction pillow main body. The cervical traction pillow main body is a flexible cervical traction pillow main body with a narrow upper part and a wide lower part, so as to form a neck brace traction portion at an upper end and a base at a lower end, a first back portion connected between the neck brace traction portion and the base, and two first side portions opposite and connected to the neck brace traction portion, the base, and the back portion. The neck brace traction portion and a bottom surface of the base are connected in an acute angle. Due to the above structure, when a user uses the cervical traction pillow for cervical traction, the heating device can generate heat and transfer the heat to the cervical vertebra of the user to accelerate the blood circulation in the cervical vertebra of the user, improve the cervical traction effect, and relieve the cervical fatigue. Furthermore, the neck traction portion and the bottom surface of the base are connected in the acute angle. This design takes the physiological curve of the human cervical vertebra into account, which helps to maintain the natural curvature of the cervical vertebra, provides support and stability, and promotes the neck health.

BRIEF DESCRIPTION OF THE DRAWINGS

In order to explain the technical solutions of the embodiments of the present disclosure more clearly, the following will briefly introduce the accompanying drawings used in the embodiments. The drawings in the following description are only some embodiments of the present disclosure. Those of ordinary skill in the art can obtain other drawings based on these drawings without creative work.

The present disclosure is further described below in detail in combination with the accompanying drawings and embodiments.

DETAILED DESCRIPTION OF THE EMBODIMENTS

Figure 1:
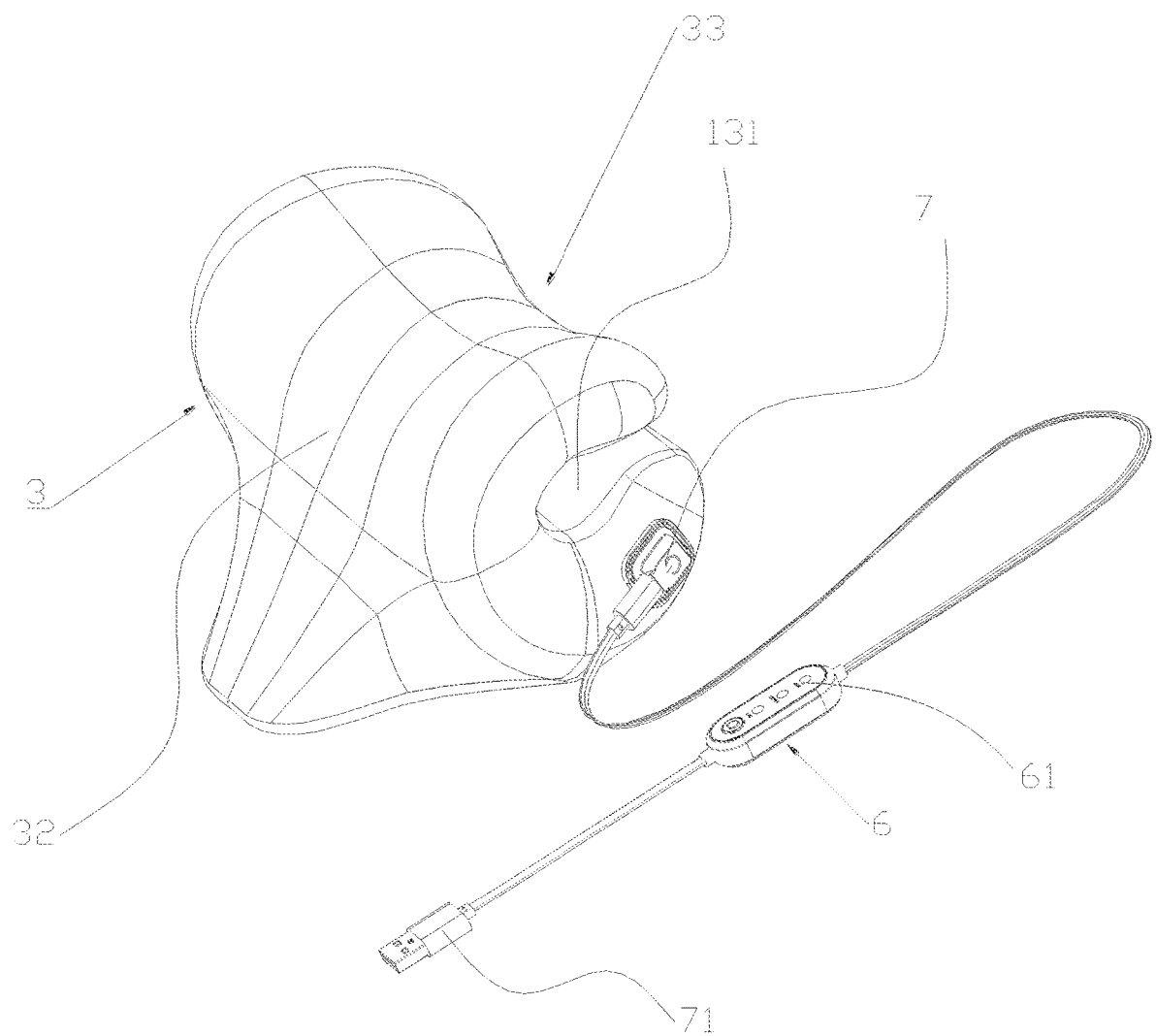
FIG. 1 is a schematic diagram of an overall structure of the present disclosure.
Figure 2:
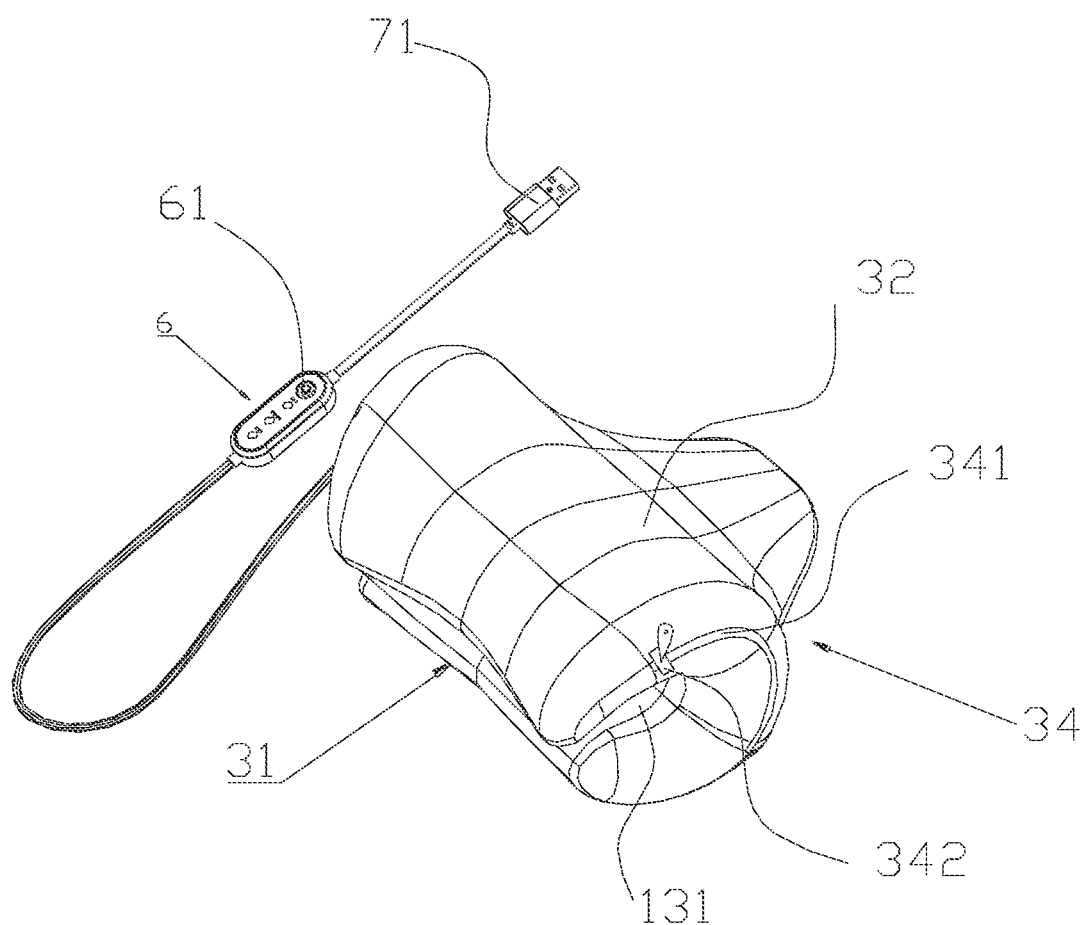
FIG. 2 is a schematic diagram of another overall structure of the present disclosure.
Figure 3:
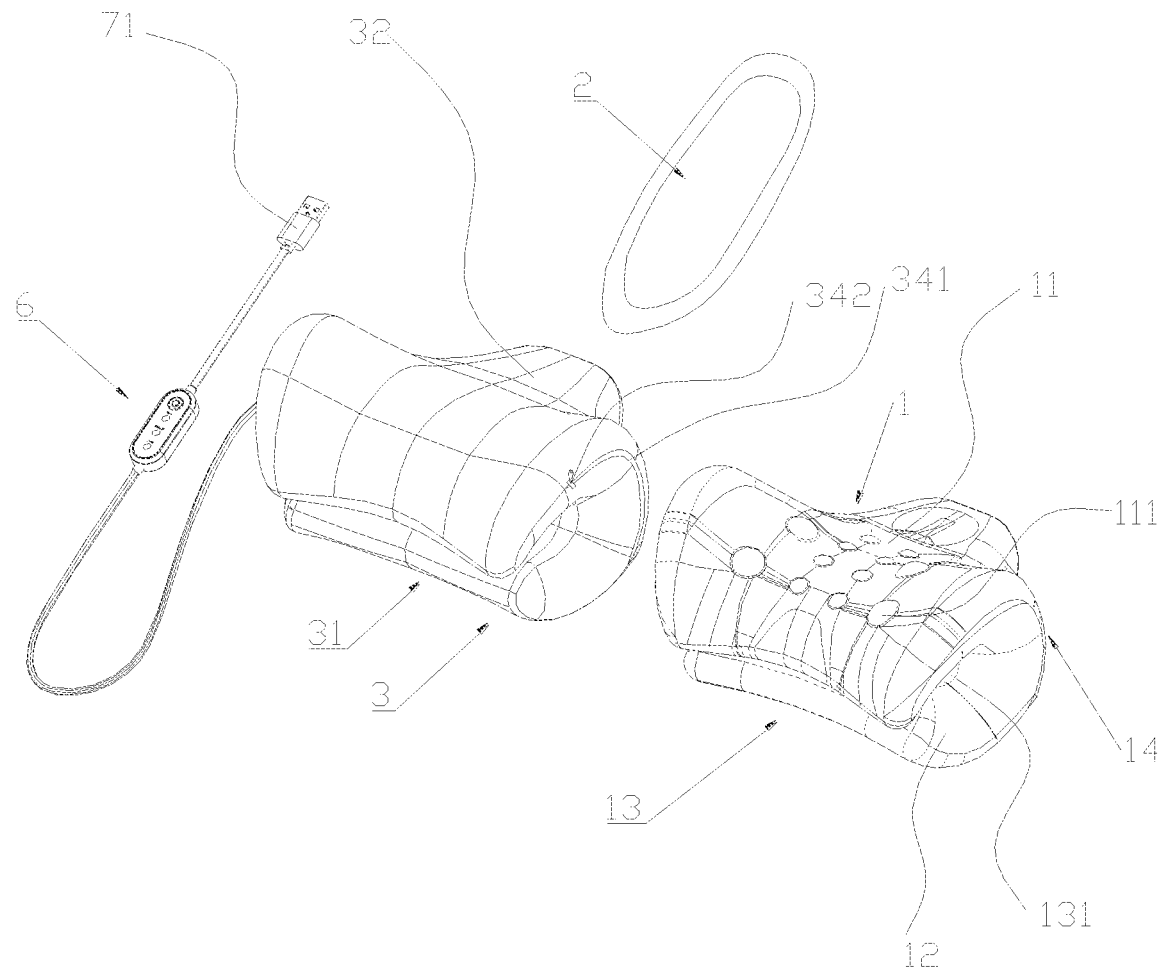
FIG. 3 is an exploded diagram of the present disclosure.
Figure 4:
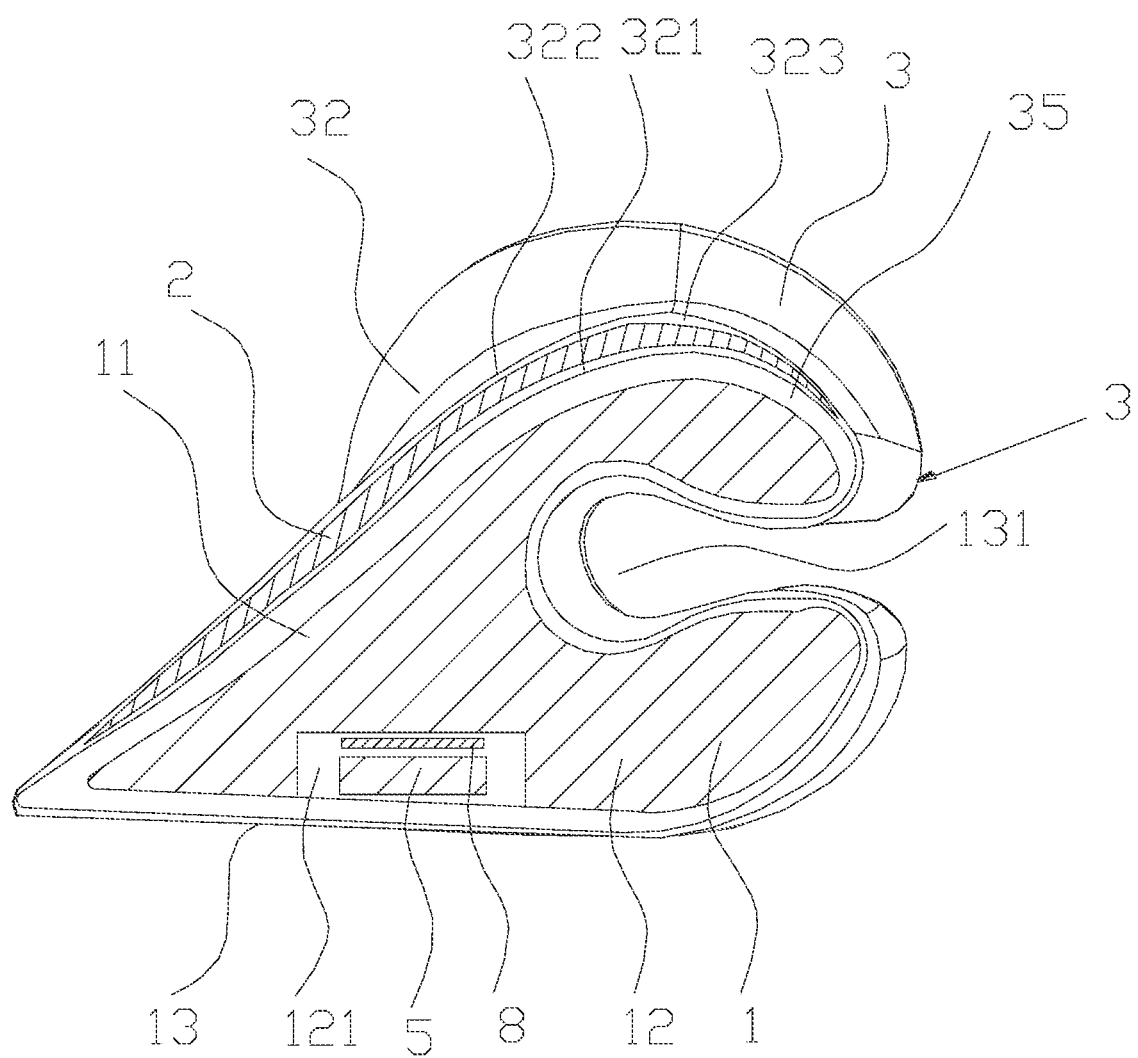
FIG. 4 is a sectional view sectioned along a heating device.

Referring to FIG. 1 to FIG. 6, a cervical traction pillow includes a cervical traction pillow main body 1 and a heating device 2. The heating device 2 covers the cervical traction pillow main body 1. The cervical traction pillow main body 1 is a flexible cervical traction pillow main body 1 with a narrow upper part and a wide lower part, so as to form a neck brace traction portion 11 at an upper end and a base 12 at a lower end, a first back portion 13 connected between the neck brace traction portion 11 and the base 12, and two first side portions 14 opposite and connected to the neck brace traction portion 11, the base 12, and the back portion. The neck brace traction portion 11 and a bottom surface of the base 12 are connected in an acute angle. Due to the above structure, when a user uses the cervical traction pillow for cervical traction, the heating device 2 can generate heat and transfer the heat to the cervical vertebra of the user to accelerate the blood circulation in the cervical vertebra of the user, improve the cervical traction effect, and relieve the cervical fatigue. Furthermore, the neck traction portion 11 and the bottom surface of the base 12 are connected in the acute angle. This design takes the physiological curve of the human cervical vertebra into account, which helps to maintain the natural curvature of the cervical vertebra, provides support and stability, and promotes the neck health.

In this embodiment, the first back portion 13 is provided with an adjustment gap 131. The adjustment gap 131 is configured to adjust an angle and distance between the neck brace traction portion 11 and the base 12, so as to adjust a height and supporting angle of the cervical traction pillow main body 1. Due to the above structure, a user can adjust the angle and distance between the neck brace traction portion 11 and the base 12 through the adjustment gap 131 to adjust the height and supporting angle of the cervical traction pillow main body 1, so that the user can enjoy cervical traction under a suitable supporting angle.

In this embodiment, the heating device 2 covers the neck brace traction portion 11. The heating device 2 can generate heat and transfer the heat to the cervical vertebra of a user to accelerate the blood circulation in the cervical vertebra of the user, improve the cervical traction effect, and relieve the cervical fatigue.

In this embodiment, the cervical traction pillow further includes a traction protective case main body 3. The traction protective case main body 3 includes a bottom portion 31, a neck brace protection portion 32 connected to the bottom portion 31, a second back portion 33 connected between the neck brace protection portion 32 and the bottom portion 31, and two second side portions 34 opposite and connected to the neck brace protection portion 32, the bottom portion 31, and the second back portion 33. The neck brace protection portion 32 and the bottom portion 31 are connected in an acute angle. Preferably, the neck brace protection portion 32 includes an inner layer 321 and an outer layer 322. A first accommodating cavity 323 is formed between the inner layer 321 and the outer layer 322. The heating device 2 is arranged in the first accommodating cavity 323 and extends from one end, close to the bottom portion 31, of the neck brace protection portion 32 to the other end, close to the second back portion 33, of the neck brace protection portion 32. Due to the above structure, as the neck brace protection portion 32 is provided with the inner layer 321 and the outer layer 322; the first accommodating cavity 323 is formed between the inner layer 321 and the outer layer 322; and the heating device 2 is arranged in the first accommodating cavity 323, so that mounting of the heating device 2 is effectively achieved. When a user uses the cervical traction pillow for cervical traction, the heating device 2 can generate heat and transfer the heat to the cervical vertebra of the user through the outer layer 322 to accelerate the blood circulation in the cervical vertebra of the user, improve the cervical traction effect, and relieve the cervical fatigue.

Further preferably, the traction protective case main body 3 is provided with a second accommodating cavity 35. The second accommodating cavity 35 fully accommodates the cervical traction pillow main body 1. The heating device 2 is arranged between the neck brace protection portion 32 and the cervical traction pillow main body 1 and extends from one end, close to the bottom portion 31, of the neck brace traction portion 11 to the other end, close to the first back portion 13, of the neck brace traction portion 11. Due to the above structure, the traction protective case main body 3 covers a surface of the cervical traction pillow main body 1, so that the cervical traction pillow main body 1 can be effectively prevented from getting dirty, and the cervical traction pillow can be prevented from breeding bacteria. Furthermore, as the heating device 2 is arranged between the traction protective case main body 3 and the cervical traction pillow main body 1, when a user uses the cervical traction pillow for cervical traction, the heating device 2 can generate heat and transfer the heat to the cervical vertebra of the user to accelerate the blood circulation in the cervical vertebra of the user, improve the cervical traction effect, and relieve the cervical fatigue.

In this embodiment, the traction protective case main body 3, the heating device 2, and the cervical traction pillow main body 1 are stacked in sequence. Due to the above structure, a user can be avoided from directly contacting a heat source, so that a safer and more comfortable experience is provided.

In this embodiment, the cervical traction pillow is further provided with a vibration device 4. The cervical traction pillow main body 1 is provided with a motor accommodating slot 15. The vibration device 4 is arranged in the motor accommodating slot 15. The vibration device 4 is configured to drive the cervical traction pillow main body 1 to vibrate to achieve a massage function. Specifically, the vibration device 4 is a polarization motor 41. The polarization motor 41 is provided with a rotating shaft 411 and an eccentric block 412. The polarization motor 41 rotates the rotating shaft 411 to drive the eccentric block 412 to ceaselessly strike an inner wall of the motor accommodating slot 15, so that the polarization motor 41 drives the cervical traction pillow main body 1 to vibrate to achieve the massage function.

Figure 5:
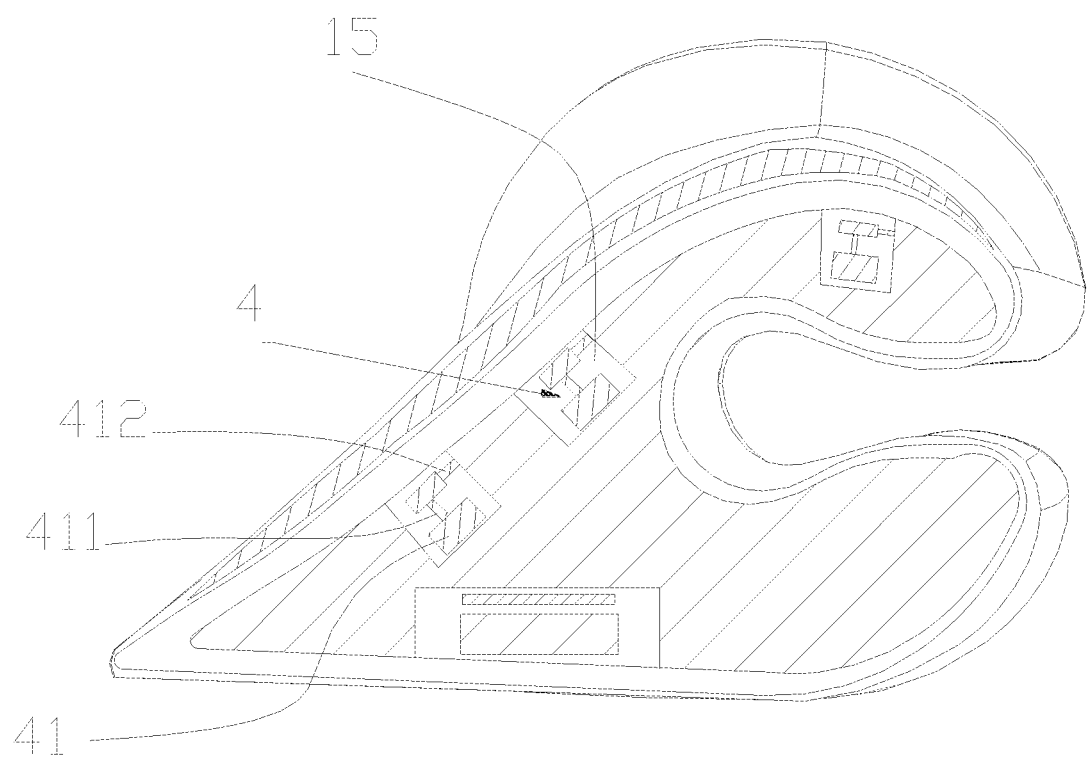
FIG. 5 is a sectional view sectioned along a vibration device.

Preferably, as shown in FIG. 5, the polarization motor 41 rotates the rotating shaft 411 to drive the eccentric block 412 to ceaselessly strike an inner side wall of the motor accommodating slot 15, so that the polarization motor 41 drives the cervical traction pillow main body 1 to vibrate to achieve the massage function.

Figure 6:
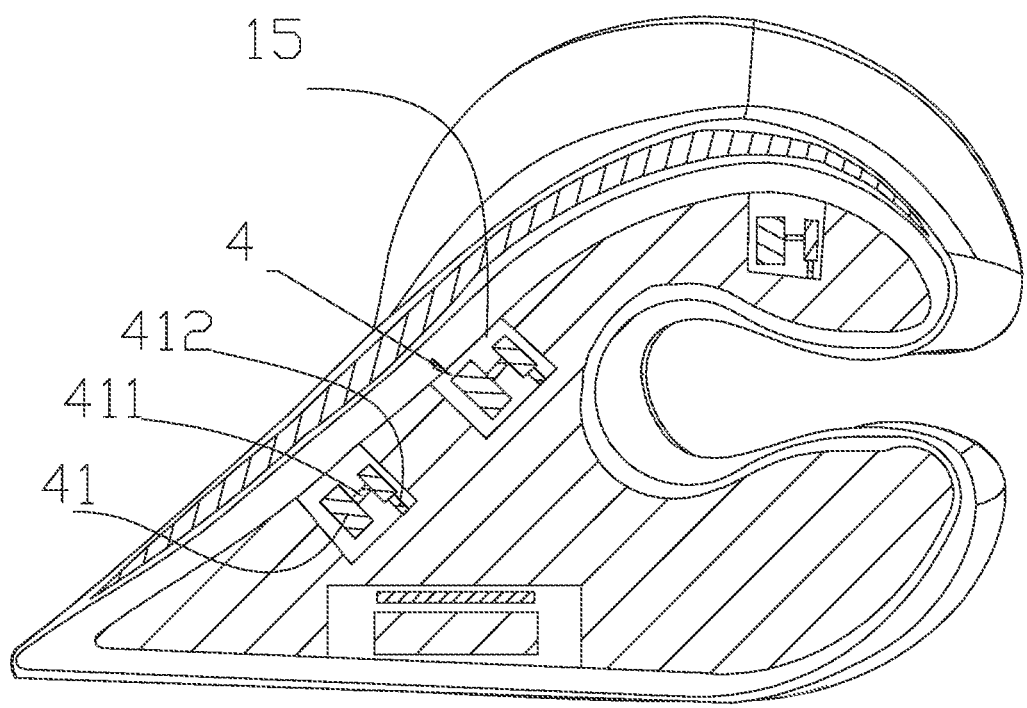
FIG. 6 is another sectional view sectioned along a vibration device.

Further preferably, as shown in FIG. 6, the polarization motor 41 rotates the rotating shaft 411 to drive the eccentric block 412 to ceaselessly strike a bottom wall of the motor accommodating slot 15, so that the polarization motor drives the cervical traction pillow main body 1 to vibrate to achieve the massage function. Due to the above structure, the polarization motor 41 is activated to rotate the rotating shaft 411. When driven by the rotating shaft 411, the eccentric block 412 rotates and ceaselessly strikes the inner wall of the motor accommodating slot 15, causing the cervical traction pillow main body 1 to ceaselessly vibrate to achieve the massage function of the cervical traction pillow. Under the action of the polarization motor 41, a user can place the neck on the cervical traction pillow, and the polarization motor 41 causes the cervical traction pillow main body 1 to vibrate. This design can accelerate the blood circulation in the cervical vertebra of the user, improve the cervical traction effect, effectively relieve the cervical fatigue, and play a massaging and soothing role.

In this embodiment, the cervical traction pillow further includes a power supply module 5. The power supply module 5 is electrically connected to the heating device 2 and the massage device 4 to supply power to the heating device 2 and the massage device 4. The traction protective case main body 3 is further provided with a power input port 7. The power input port 7 is electrically connected to the massage device 4 and the heating device 2 to supply power to the massage device 4 and the heating device 2. The power input port 7 is arranged on one side portion of the two second side portions 34. The neck brace traction portion 11 is provided with several massage convex points 111. A power supply accommodating slot 121 is arranged in the base 12. The power supply module 5 is arranged in the power supply accommodating slot 121. The power input port 7 is a TYPE C power input port 71, or a USB power input port 71, or other types of power input ports. Due to the above structure, the power input port 7 can supply power to the heating device 2 and the massage device 4, and the power supply module 5 can be also charged by means of the power input port 7, so that the heating device 2 of the cervical traction pillow can be powered by mains supply or the power supply module 5. When the mains supply is cut off or a user needs to go out with the cervical traction pillow covered with a protective case of the cervical traction pillow, the heating device 2 is powered by the power supply module 5, so that the user can enjoy the heating function of the heating device 2 during cervical traction, so as to accelerate the blood circulation in the cervical vertebra of the user, improve the cervical traction effect, and relieve the cervical fatigue. The power supply module 5 can be a lithium battery or other types of batteries.

In this embodiment, the cervical traction pillow is further provided with a temperature control device 6. The temperature control device 6 is electrically connected with the heating device 2. The temperature control device 6 is configured to control a surface temperature of the heating device 2. Specifically, the temperature control device 6 is a temperature control switch 61. The temperature control switch 61 is configured to control a current flowing through the heating device 2 to control the surface temperature of the heating device 2. The cervical traction pillow further includes a wireless communication module 8. The wireless communication module 8 is electrically connected with the temperature control device 6 to receive a wireless temperature control signal and control the surface temperature of the heating device 2. Due to the above structure, a user can control the surface temperature of the heating device through the temperature control switch 61. In addition, by the arrangement of the wireless communication module 8, the user can also send a wireless temperature control signal to the temperature control switch 61 through a remote controller, a mobile phone, or other mobile terminal devices, so that the temperature control switch 61 receives the wireless temperature control signal and controls the surface temperature of the heating device to achieve a remote wireless temperature adjustment function.

In this embodiment, the back portion of the cervical traction pillow main body 1 is of a "C"-shaped structure, and the back portion of the traction protective case main body 3 is of a "C"-shaped structure. Due to the above structure, the cervical traction pillow with the "C"-shaped back portion satisfies the physiological curve of the human cervical vertebra, and is beautiful.

In this embodiment, the traction protective case main body 3 sleeves and covers a surface of the cervical traction pillow main body 1 through a sleeving opening 341 located on one of the two second side portions 34. A zipper 342 for opening or closing the sleeving opening is arranged at the sleeving opening 341. Due to the above structure, a user can open the sleeving opening 341 with the zipper 342, and conveniently sleeve and cover the surface of the cervical traction pillow with the traction protective case main body 3. After the sleeving is completed, the sleeving opening 341 can be closed with the zipper 342 to prevent the traction protective case main body 3 from being separated from the surface of the cervical traction pillow. The cervical traction pillow has a simple structure and stable connection, so that it is convenient for the user to mount, replace and clean the traction pillow protective case main body. Further, the heating device 2 is arranged on the traction protective case main body 3, so that when the cervical traction pillow main body 1 is damaged or aged and needs to be replaced, the sleeving opening 341 can be opened with the zipper 342, and it is convenient for a user to remove the traction protective case main body provided with the heating device 2 from the surface of the cervical traction pillow, and to sleeve a new traction pillow main body 1 with the traction protective case main body 3 provided with the heating device, thus achieving repeated use of the traction protective case main body 3 and the heating device 2, which reduces the use cost of the user and is more environmentally friendly.

In this embodiment, the heating device 2 is a graphene heating sheet or a carbon fiber heating sheet or a composite fiber heating piece. The heating device 2 is the graphene heating sheet or the carbon fiber heating sheet or the composite fiber heating piece, so that compared with a metal heating wire on the market, the graphene heating sheet, the carbon fiber heating sheet and the composite fiber heating piece generates heat immediately after being powered on, without preheating, have high heating efficiency and uniform heat, and can quickly generate heat and transfer it to the cervical vertebra of the user through the neck brace protection portion and the neck brace traction portion. The composite fiber heating wire is a metal fiber heating wire mainly prepared from iron, steel, nickel and the like. A metal is made to be wirelike by a special process and is then stranded into a rope. The carbon fiber heating wire which is mainly prepared from carbon accounting for 99% is nonmetal, belonging to a semiconductor. An electric heating principle of the carbon fiber heating wire is mainly generating heat energy by mutual collision of electric ions generated after the carbon fiber heating wire is powered on.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

What is claimed is:

1. A cervical traction pillow, comprising a cervical traction pillow main body, a heating device and a traction protective case main body,
    wherein the heating device covers the cervical traction pillow main body; the cervical traction pillow main body is a flexible cervical traction pillow main body with a narrow upper part and a wide lower part, so as to form a neck brace traction portion at an upper end and a base at a lower end, a first back portion connected between the neck brace traction portion and the base, and two first side portions opposite and connected to the neck brace traction portion, the base, and the back portion; and the neck brace traction portion and a bottom surface of the base are connected in an acute angle;
    wherein the traction protective case main body comprises a bottom portion, a neck brace protection portion connected to the bottom portion, a second back portion connected between the neck brace protection portion and the bottom portion, and two second side portions opposite and connected to the neck brace protection portion, the bottom portion, and the second back portion; and the neck brace protection portion and the bottom portion are connected in an acute angle.

2. The cervical traction pillow according to claim 1, wherein the first back portion is provided with an adjustment gap; and the adjustment gap is configured to adjust an angle and distance between the neck brace traction portion and the base, so as to adjust a height and supporting angle of the cervical traction pillow main body.

3. The cervical traction pillow according to claim 1, wherein the heating device covers the neck brace traction portion.

4. The cervical traction pillow according to claim 1, wherein the neck brace protection portion comprises an inner layer and an outer layer; a first accommodating cavity is formed between the inner layer and the outer layer; the neck brace protection portion comprises a first end close to the bottom portion and a second end close to the second back portion, and the heating device is arranged in the first accommodating cavity and extends from the first end to the second end.

5. The cervical traction pillow according to claim 1, wherein the traction protective case main body is provided with a second accommodating cavity; the second accommodating cavity fully accommodates the cervical traction pillow main body; the neck brace protection portion comprises a first end close to the bottom portion and a second end close to the second back portion, the heating device is arranged between the neck brace protection portion and the cervical traction pillow main body and extends from the first end to the second end.

6. The cervical traction pillow according to claim 5, wherein the traction protective case main body, the heating device, and the cervical traction pillow main body are stacked in sequence.

7. The cervical traction pillow according to claim 1, wherein the cervical traction pillow is further provided with a vibration device; the cervical traction pillow main body is provided with a motor accommodating slot; the vibration device is arranged in the motor accommodating slot; and the vibration device is configured to drive the cervical traction pillow main body to vibrate to achieve a massage function.

8. The cervical traction pillow according to claim 7, wherein the vibration device is a polarization motor; the polarization motor is provided with a rotating shaft and an eccentric block; and the polarization motor rotates the rotating shaft to drive the eccentric block to ceaselessly strike an inner wall of the motor accommodating slot, so that the polarization motor drives the cervical traction pillow main body to vibrate to achieve the massage function.

9. The cervical traction pillow according to claim 8, wherein the polarization motor rotates the rotating shaft to drive the eccentric block to ceaselessly strike an inner side wall of the motor accommodating slot, so that the polarization motor drives the cervical traction pillow main body to vibrate to achieve the massage function.

10. The cervical traction pillow according to claim 8, wherein the polarization motor rotates the rotating shaft to drive the eccentric block to ceaselessly strike a bottom wall of the motor accommodating slot, so that the polarization motor drives the cervical traction pillow main body to vibrate to achieve the massage function.

11. The cervical traction pillow according to claim 7, further comprising a power supply module, wherein the power supply module is electrically connected to the heating device and the vibration device to supply power to the heating device and the vibration device.

12. The cervical traction pillow according to claim 11, further comprising a temperature control device, wherein the temperature control device is electrically connected with the heating device; the temperature control device is configured to control a surface temperature of the heating device; the temperature control device is a temperature control switch; and the temperature control switch is configured to control a current flowing through the heating device to control the surface temperature of the heating device.

13. The cervical traction pillow according to claim 12, wherein the traction protective case main body is further provided with a power input port; the power input port is electrically connected to the vibration device and the heating device to supply power to the vibration device and the heating device; and the power input port is arranged on one side portion of the two second side portions.

14. The cervical traction pillow according to claim 13, further comprising a wireless communication module, wherein the wireless communication module is electrically connected with the temperature control device to receive a wireless temperature control signal and control the surface temperature of the heating device.

15. The cervical traction pillow according to claim 14, wherein the neck brace traction portion is provided with several massage convex points; a power supply accommodating slot is arranged in the base; and the power supply module is arranged in the power supply accommodating slot.

16. The cervical traction pillow according to claim 15, wherein the back portion of the cervical traction pillow main body is of a "C"-shaped structure.

17. The cervical traction pillow according to claim 16, wherein the back portion of the traction protective case main body is of a "C"-shaped structure.

18. The cervical traction pillow according to claim 17, wherein the traction protective case main body sleeves and covers a surface of the cervical traction pillow main body through a sleeving opening located on one of the two second side portions; and a zipper for opening or closing the sleeving opening is arranged at the sleeving opening.

19. The cervical traction pillow according to claim 1, wherein the heating device is a graphene heating sheet or a carbon fiber heating sheet or a composite fiber heating piece.

* * * * *